US012697224B2

(12) United States Patent
Zhao et al.

(10) Patent No.: US 12,697,224 B2
(45) Date of Patent: Aug. 4, 2026

(54) SURGICAL UPPER COMPUTER FOR TOTAL KNEE ARTHROPLASTY, AND TOTAL KNEE ARTHROPLASTY SYSTEM

(71) Applicant: TINAVI MEDICAL TECHNOLOGIES CO., LTD., Beijing (CN)

(72) Inventors: Yongqiang Zhao, Beijing (CN); Hongwei Shi, Beijing (CN); Yixin Zhou, Beijing (CN); Dejin Yang, Beijing (CN); Ye Tian, Beijing (CN); Bo Chen, Beijing (CN)

(73) Assignee: TINAVI MEDICAL TECHNOLOGIES CO., LTD., Beijing (CN)

( * ) Notice: Subject to any disclaimer, the term of this patent is extended or adjusted under 35 U.S.C. 154(b) by 827 days.

(21) Appl. No.: 17/891,670

(22) Filed: Aug. 19, 2022

(65) Prior Publication Data

US 2023/0181326 A1 Jun. 15, 2023

(30) Foreign Application Priority Data

Dec. 14, 2021 (CN) .......................... 202111529252.X

(51) Int. Cl.
*A61F 2/38* (2006.01)
*A61B 17/02* (2006.01)
(Continued)

(52) U.S. Cl.
CPC ............ *A61F 2/38* (2013.01); *A61B 17/1764* (2013.01); *A61B 17/025* (2013.01); (Continued)

(58) Field of Classification Search
CPC ... A61B 17/025; A61B 17/17; A61B 17/1764; A61B 17/154; A61B 2017/564; (Continued)

(56) References Cited

U.S. PATENT DOCUMENTS 10,285,683 B2 * 5/2019 Plaskos ................. A61B 34/10
2005/0234332 A1 10/2005 Murphy
(Continued)

FOREIGN PATENT DOCUMENTS

CN 107582167 A 1/2018
CN 109640862 A 4/2019
(Continued)

OTHER PUBLICATIONS

Office Action issued on Jul. 1, 2025, in corresponding Chinese Application No. 202111529252.X, 3 pages.
(Continued)

*Primary Examiner* — Marcela I. Shirsat
(74) *Attorney, Agent, or Firm* — Scully, Scott, Murphy & Presser, P.C.

(57) ABSTRACT

A surgical upper computer for a total knee arthroplasty, and a total knee arthroplasty system, and in the field of surgical equipment. The surgical upper computer includes a memory storing a first computer program which enables a processor to execute a first operating mode of the surgical upper computer, where the first operating mode includes: exhibiting, by an interactive interface, to a user, first information to be input, the first information including a magnitude range and change interval of a pushing force applied between a femur and a tibia; in response to user input, controlling a butting member and a push plate to apply different pushing forces at a preset joint flexion angle, and acquiring relationship data between the pushing force and a gap; and displaying the relationship data. Accordingly, the force and gap between soft tissues in the total knee arthroplasty can be acquired and displayed.

9 Claims, 11 Drawing Sheets

Exhibit, by means of an interactive interface, to a user a magnitude range and change interval of a pushing force applied between a femur and a tibia ⌐-~S101

In response to information input by the user, control a butting member and a push plate to apply different pushing forces between the femur and the tibia at a preset joint flexion angle, and acquire corresponding relationship data between the pushing force and a gap between the femur and the tibia ⌐-~S103

Visually exhibit the corresponding relationship data ⌐-~S105

(51) Int. Cl.

| | |
|---|---|
| *A61B 17/15* | (2006.01) |
| *A61B 17/17* | (2006.01) |
| *A61B 17/56* | (2006.01) |
| *A61B 34/00* | (2016.01) |
| *A61B 34/10* | (2016.01) |
| *A61B 34/20* | (2016.01) |
| *A61B 34/30* | (2016.01) |
| *A61B 90/00* | (2016.01) |
| *A61F 2/46* | (2006.01) |

(52) U.S. Cl.

CPC ..... *A61B 2017/0268* (2013.01); *A61B 17/154* (2013.01); *A61B 2017/564* (2013.01); *A61B 34/10* (2016.02); *A61B 2034/101* (2016.02); *A61B 2034/102* (2016.02); *A61B 2034/104* (2016.02); *A61B 2034/105* (2016.02); *A61B 2034/107* (2016.02); *A61B 2034/108* (2016.02); *A61B 34/20* (2016.02); *A61B 2034/2048* (2016.02); *A61B 34/25* (2016.02); *A61B 34/30* (2016.02); *A61B 2090/064* (2016.02); *A61B 2090/067* (2016.02); *A61B 2562/0219* (2013.01); *A61F 2/3886* (2013.01); *A61F 2/461* (2013.01); *A61F 2002/4632* (2013.01); *A61F 2002/4633* (2013.01); *A61F 2/4657* (2013.01); *A61F 2002/4666* (2013.01); *A61F 2002/4667* (2013.01); *A61F 2002/4668* (2013.01)

(58) Field of Classification Search

CPC ...... A61B 2017/0268; A61B 2090/061; A61B 2090/064; A61B 2090/067; A61B 34/10; A61B 34/25; A61B 34/20; A61B 34/30; A61B 2034/2048; A61B 2034/101; A61B 2034/102; A61B 2034/104; A61B 2034/105; A61B 2034/107; A61B 2034/108; A61B 2562/0219; A61F 2/46; A61F 2/4657; A61F 2/38; A61F 2/3886; A61F 2/4603; A61F 2/461; A61F 2002/4632; A61F 2002/4666; A61F 2002/4668; A61F 2002/4658; A61F 2002/4633; A61F 2002/4667; G16H 20/40

USPC ..................................................... 606/88, 90

See application file for complete search history.

(56) References Cited

U.S. PATENT DOCUMENTS

| | | | |
|---|---|---|---|
| 2010/0249791 A1 | 9/2010 | Roche | |
| 2013/0013076 A1 | 1/2013 | Fisher et al. | |
| 2016/0278754 A1* | 9/2016 | Todorov | .............. A61B 17/025 |

FOREIGN PATENT DOCUMENTS

| | | | |
|---|---|---|---|
| CN | 110638476 A | 1/2020 | |
| CN | 111249002 A | 6/2020 | |
| CN | 111685771 A | 9/2020 | |
| CN | 111759312 A | 10/2020 | |
| CN | 212438814 U | 2/2021 | |
| CN | 112914726 A | 6/2021 | |
| CN | 113116353 A | 7/2021 | |
| CN | 113440317 A | 9/2021 | |

OTHER PUBLICATIONS

Search Report issued on Jun. 19, 2025, in corresponding Chinese Application No. 202111529252.X, 7 pages.

Search Report issued on Sep. 28, 2022, in corresponding International Application No. PCT/CN2022/104787, 6 pages.

* cited by examiner

Exhibit, by means of an interactive interface, to a user a magnitude range and change interval of a pushing force applied between a femur and a tibia ⌐S101

In response to information input by the user, control a butting member and a push plate to apply different pushing forces between the femur and the tibia at a preset joint flexion angle, and acquire corresponding relationship data between the pushing force and a gap between the femur and the tibia ⌐S103

Visually exhibit the corresponding relationship data ⌐S105

FIG. 2

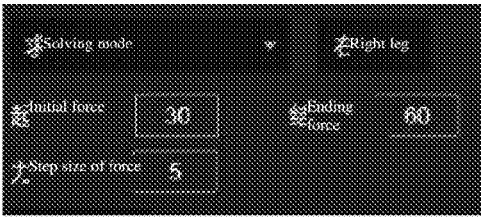

FIG. 3A

Exhibit, by means of the interactive interface, to the user a plurality of value ranges of the joint flexion angle and data values, corresponding to the plurality of value ranges, of a pushing force applied between a femur and a tibia that are subjected to a pre-cut osteotomy ⟶S201

In response to information input by the user, control the butting member and the push plate to apply corresponding pushing forces between the femur and the tibia respectively within the plurality of value ranges of the joint flexion angle, and acquire data values of gaps between the femur and the tibia ⟶S203

Visually exhibit a relationship between the data values of the pushing force and the joint flexion angle and a relationship between the data values of the gap and the joint flexion angle ⟶S205

FIG. 4

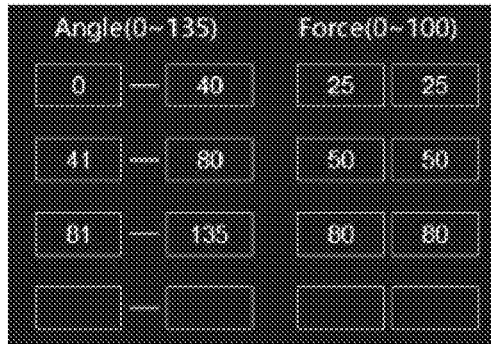

FIG. 5A

Exhibit, by means of the interactive interface, to the user a plurality of value ranges of the joint flexion angle and data values, corresponding to the plurality of value ranges, of preset gaps formed between the femur and the tibia that are subjected to the pre-cut osteotomy ⟵ S301

In response to information input by the user, control the butting member and the push plate to form corresponding gaps between the femur and the tibia respectively within the plurality of value ranges of the joint flexion angle, and acquire data values of the pushing forces between the femur and the tibia ⟵ S303

Visually exhibit a relationship between the data values of the pushing force and the joint flexion angle and a relationship between the data values of the gap and the joint flexion angle ⟵ S305

FIG. 6

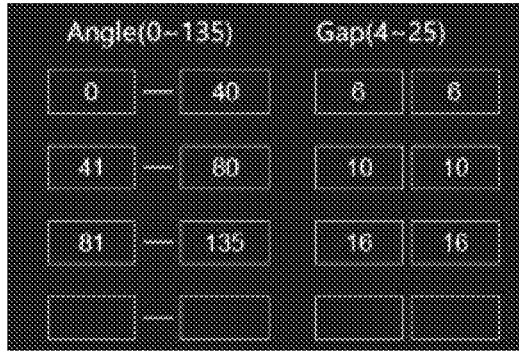

FIG. 7A

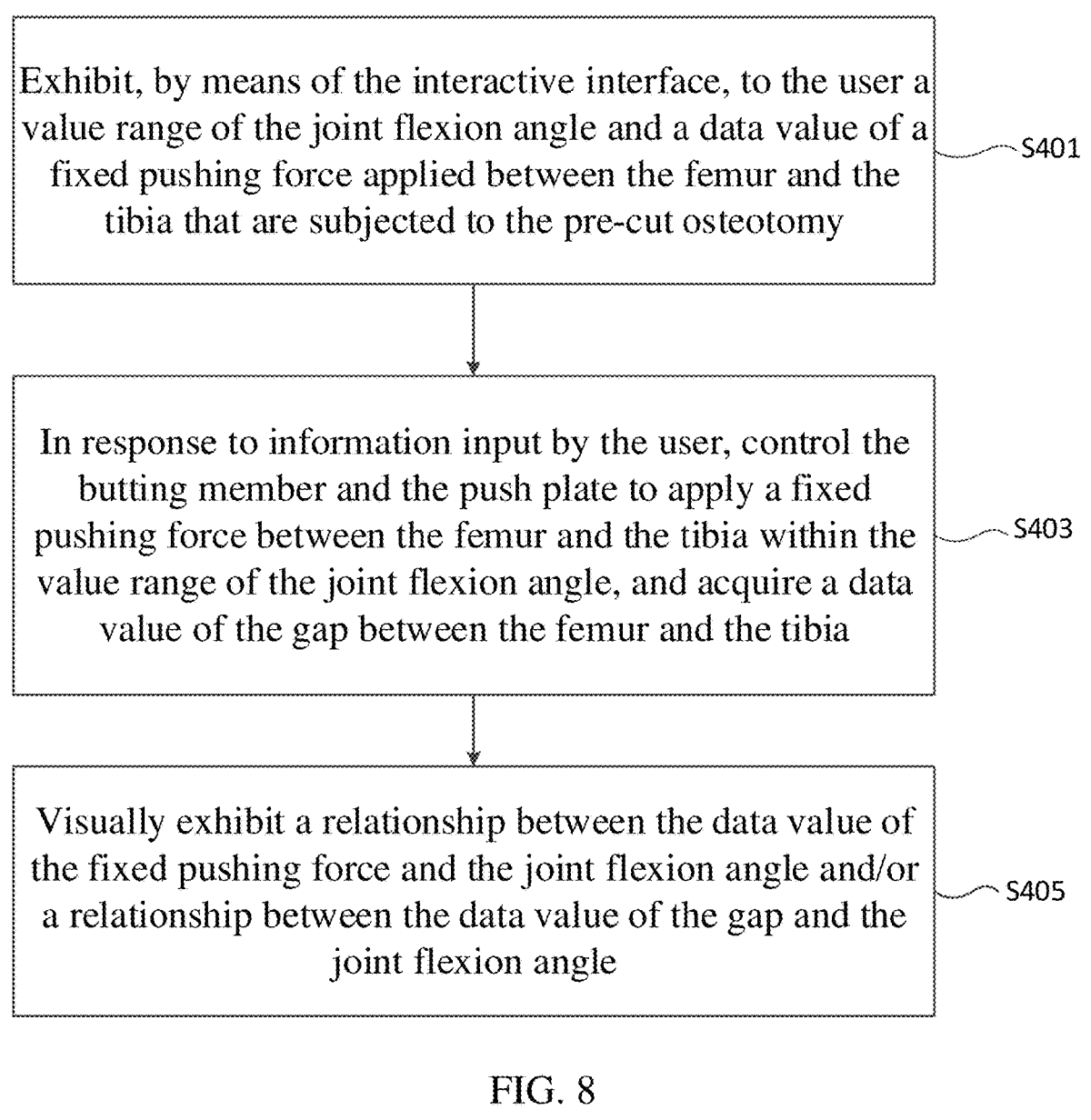

Exhibit, by means of the interactive interface, to the user a value range of the joint flexion angle and a data value of a fixed pushing force applied between the femur and the tibia that are subjected to the pre-cut osteotomy    ~S401

In response to information input by the user, control the butting member and the push plate to apply a fixed pushing force between the femur and the tibia within the value range of the joint flexion angle, and acquire a data value of the gap between the femur and the tibia    ~S403

Visually exhibit a relationship between the data value of the fixed pushing force and the joint flexion angle and/or a relationship between the data value of the gap and the joint flexion angle    ~S405

FIG. 8

Figure 10:
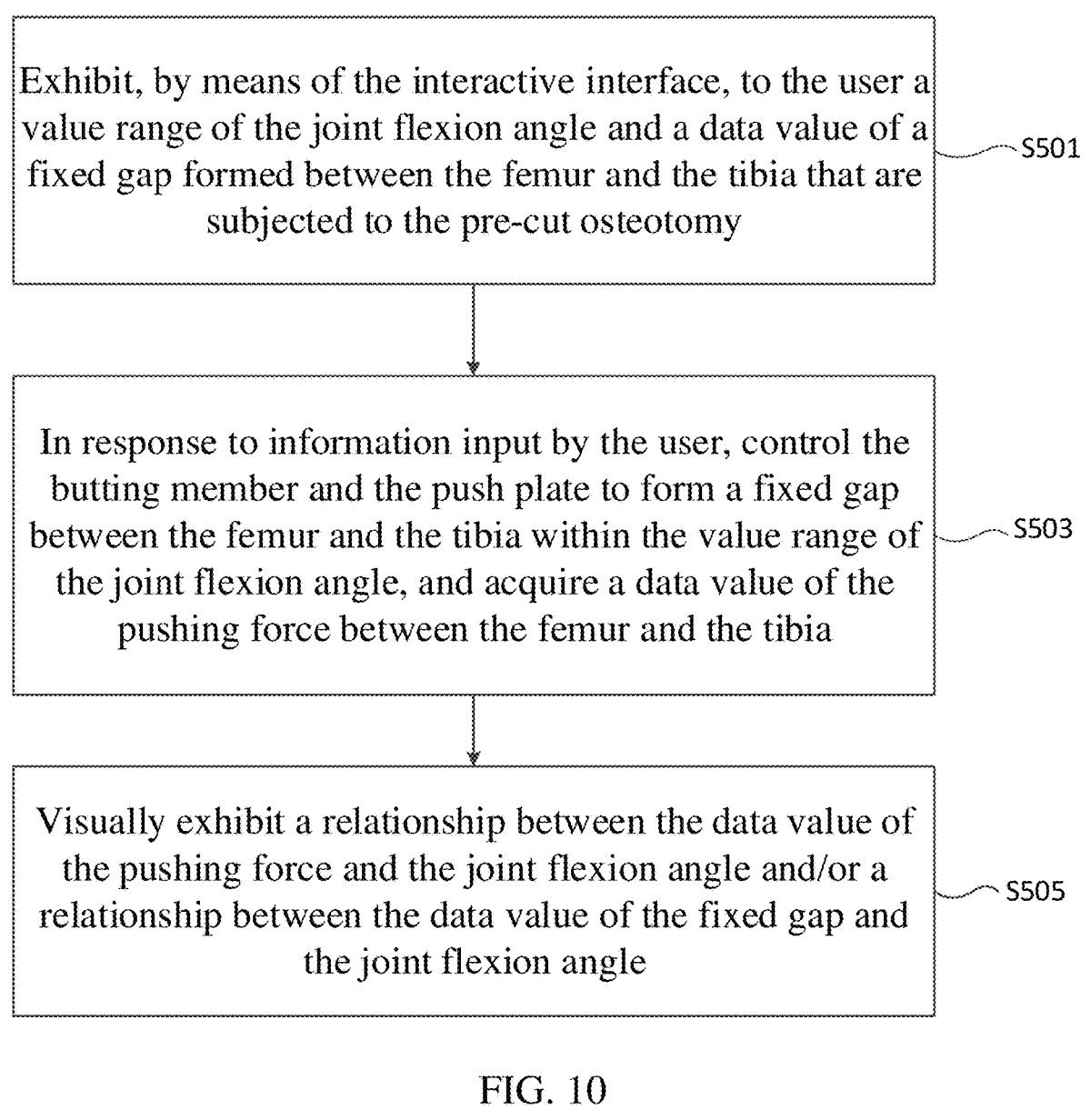

Exhibit, by means of the interactive interface, to the user a value range of the joint flexion angle and a data value of a fixed gap formed between the femur and the tibia that are subjected to the pre-cut osteotomy

~S501

In response to information input by the user, control the butting member and the push plate to form a fixed gap between the femur and the tibia within the value range of the joint flexion angle, and acquire a data value of the pushing force between the femur and the tibia

~S503

Visually exhibit a relationship between the data value of the pushing force and the joint flexion angle and/or a relationship between the data value of the fixed gap and the joint flexion angle

SURGICAL UPPER COMPUTER FOR TOTAL KNEE ARTHROPLASTY, AND TOTAL KNEE ARTHROPLASTY SYSTEM

TECHNICAL FIELD

The present application relates to the field of surgical equipments, and in particular, relates to a surgical upper computer for a total knee arthroplasty, and a total knee arthroplasty system.

BACKGROUND

Total knee arthroplasty (TKA) is a complicated orthopedic operation due to the complex composition of a knee joint, which includes a femur, a tibia, ligaments surrounding the joint, as well as muscles, cartilages, etc.

As one of the main approaches to the treatment of degenerative knee joint diseases, TKA has a surgical goal of restoring the alignment of a lower limb and the range of motion of a joint, thereby maintaining joint stability and reducing pains. Appropriate prosthesis alignment and soft tissue balance are keys to achieving the surgical goal.

In a traditional TKA, osteotomy is typically performed on the femur and tibia by using a method combining intramedullary and extramedullary positioning and gap balancing, and then, ligaments are released to achieve a tension balance. In actual operations, the traditional TKA largely depends on the feeling and experience of a surgeon, and presents a risk of insufficient or excessive release, which would in turn lead to complications such as joint instability, limited joint movement or abnormal joint movement in a patient.

Releasing the ligaments is in effect a kind of damage to a human tissue structure. If the magnitude of soft tissue tension can be understood during a surgery, a proper adjustment would be made based on the tension during the osteotomy, such that no or few ligaments will be released after the fitting of a prosthesis, thereby protecting soft tissues.

SUMMARY

The present application provides a surgical upper computer for a total knee arthroplasty, and a total knee arthroplasty system, whereby corresponding relationship data of forces and gaps between the femur and the tibia is acquired by means of different operating modes and can be visually exhibited, such that a surgeon can quickly determine whether soft tissues are balanced according to the data or visualized information, and make an intraoperative adjustment.

According to one aspect of the present application, a surgical upper computer is provided for controlling a knee-joint soft tissue balance measurement apparatus and performing data acquisition in a total knee arthroplasty, wherein the measurement apparatus comprises a master machine and an accessory, the master machine comprises a butting member respectively acting on distal medial and lateral condyles of a femur and a push plate supporting a tibia, the surgical upper computer comprises: a processor, and a memory storing a first computer program which, when executed by the processor, enables the processor to execute a first operating mode of the surgical upper computer, and the first operating mode comprises: exhibiting, by means of an interactive interface, to a user first information to be input, the first information to be input comprising a magnitude range and change interval of a pushing force applied between a femur and a tibia; in response to information input by the user, controlling the butting member and the push plate to apply different pushing forces between the femur and the tibia at a preset joint angle, and acquiring corresponding relationship data between the pushing force and a gap between the femur and the tibia; and visually exhibiting the corresponding relationship data.

According to some embodiments, the information to be input comprising the magnitude range and change interval of the pushing force applied between the femur and the tibia, comprises: a magnitude range and change interval of a pushing force applied between a femur and a tibia that are subjected to a pre-cut osteotomy; and a magnitude range and change interval of a pushing force applied between a femur and a tibia after prosthesis implantation and before spacer implantation.

According to some embodiments, controlling the butting member and the push plate to apply the different pushing forces between the femur and the tibia at the preset joint angle, comprises: controlling the butting member and the push plate to apply different pushing forces between the femur and the tibia respectively at a plurality of different preset joint angles.

According to some embodiments, the corresponding relationship data comprises difference values between the pushing forces and corresponding difference values and absolute values of the gaps.

According to some embodiments, the memory further stores a second computer program which, when executed by the processor, enables the processor to execute a second operating mode of the surgical upper computer, and the second operating mode comprises: exhibiting, by means of a second interactive interface, to the user second information to be input, the second information to be input comprising a dynamic change range of the preset joint flexion angle, and a relationship between the preset joint flexion angle and the pushing force applied between the femur and the tibia; in response to information input by the user, controlling the butting member and the push plate to apply corresponding pushing forces between the femur and the tibia during the process of dynamically adjusting the joint flexion angle within the dynamic change range, and acquiring data values of the gap between the femur and the tibia; and at least visually exhibiting a relationship between the data value of the gap and the joint flexion angle.

According to some embodiments, the dynamic change range of the preset joint flexion angle, and a relationship between the preset joint flexion angle and the pushing force applied between the femur and the tibia, comprise: a plurality of value ranges set according to the dynamic change range, and data values of the pushing force, corresponding to the plurality of value ranges; or the dynamic change range of the preset joint flexion angle, and a functional relationship between the preset joint flexion angle and the pushing force.

According to some embodiments, when a plurality of value ranges are set according to the dynamic change range of the preset joint flexion angle, the pushing forces corresponding to different value ranges of the preset joint flexion angle have different data values.

According to some embodiments, the memory further stores a third computer program which, when executed by the processor, enables the processor to execute a third operating mode of the surgical upper computer, and the third operating mode comprises: exhibiting, by means of a third interactive interface, to the user third information to be input, the third information to be input comprising the dynamic change range of the preset joint flexion angle, and a relationship between the preset joint flexion angle and a preset gap formed between the femur and the tibia; in response to information input by the user, controlling the butting member and the push plate to form corresponding gaps between the femur and the tibia during the process of dynamically adjusting the joint flexion angle within the dynamic change range, and acquiring a data value of the pushing force between the femur and the tibia; and at least visually exhibiting a relationship between the data value of the pushing force and the joint flexion angle.

According to some embodiments, the dynamic change range of the preset joint flexion angle, and the relationship between the preset joint flexion angle and the present gap formed between the femur and the tibia, comprise: a plurality of value ranges set according to the dynamic change range, and data values of the gap, corresponding to the plurality of value ranges; or the dynamic change range of the preset joint flexion angle, and a functional relationship between the preset joint flexion angle and the present gap.

According to some embodiments, when a plurality of value ranges are set according to the dynamic change range of the joint flexion angle, the gaps corresponding to different value ranges of the preset joint flexion angle have different data values.

According to some embodiments, the memory further stores a fourth computer program which, when executed by the processor, enables the processor to execute a fourth operating mode of the surgical upper computer, and the fourth operating mode comprises: exhibiting, by means of a fourth interactive interface, to the user fourth information to be input, the fourth information to be input comprising the dynamic change range of the preset joint flexion angle, and a data value of a fixed pushing force applied between the femur and the tibia; in response to information input by the user, controlling the butting member and the push plate to apply the fixed pushing force between the femur and the tibia during the process of dynamically adjusting the joint flexion angle within the dynamic change range, and acquiring a data value of the gap between the femur and the tibia; and at least visually exhibiting a relationship between the data value of the gap and the joint flexion angle.

According to some embodiments, the memory further stores a fifth computer program which, when executed by the processor, enables the processor to execute a fifth operating mode of the surgical upper computer, and the fifth operating mode comprises: exhibiting, by means of a fifth interactive interface, to the user fifth information to be input, the fifth information to be input comprising the dynamic change range of the preset joint flexion angle, and a data value of a fixed gap formed between the femur and the tibia; in response to information input by the user, controlling the butting member and the push plate to form the fixed gap between the femur and the tibia during the process of dynamically adjusting the joint flexion angle within the dynamic change range, and acquiring a data value of the pushing force between the femur and the tibia; and at least visually exhibiting a relationship between the data value of the pushing force and the joint flexion angle.

According to one aspect of the present application, a total knee arthroplasty system is provided, comprising the surgical upper computer as previously defined.

According to the embodiments of the present application, the angle, force and gap in the knee joint can be quantified and reasonably exhibited to facilitate the surgical operation of a surgeon and reduce the damage to a patient caused by ligament releasing.

It should be understood that the general description above and the detailed description below are merely exemplary, and are not intended to limit the present application.

BRIEF DESCRIPTION OF THE DRAWINGS

To describe the technical solutions in the embodiments of the present application more clearly, the following briefly introduces the accompanying drawings to be used in the description of the embodiments. Obviously, the accompanying drawings in the following description show merely some embodiments of the present application.

FIG. 2 illustrates a flow chart of a first operating mode of a surgical upper computer according to an exemplary embodiment of the present application;

FIG. 3A illustrates a diagram exhibiting an interactive interface of a first operating mode of a surgical upper computer according to an exemplary embodiment of the present application;

FIG. 4 illustrates a flow chart of a second operating mode of a surgical upper computer according to an exemplary embodiment of the present application;

FIG. 5A illustrates a diagram exhibiting an interactive interface of a second operating mode of a surgical upper computer according to an exemplary embodiment of the present application;

FIG. 6 illustrates a flow chart of a third operating mode of a surgical upper computer according to an exemplary embodiment of the present application;

FIG. 7A illustrates a diagram exhibiting an interactive interface of a third operating mode of a surgical upper computer according to an exemplary embodiment of the present application;

FIG. 8 illustrates a flow chart of a fourth operating mode of a surgical upper computer according to an exemplary embodiment of the present application;

FIG. 10 illustrates a flow chart of a fifth operating mode of a surgical upper computer according to an exemplary embodiment of the present application;

DETAILED DESCRIPTION OF THE EMBODIMENTS

Figures 1A, 1B:
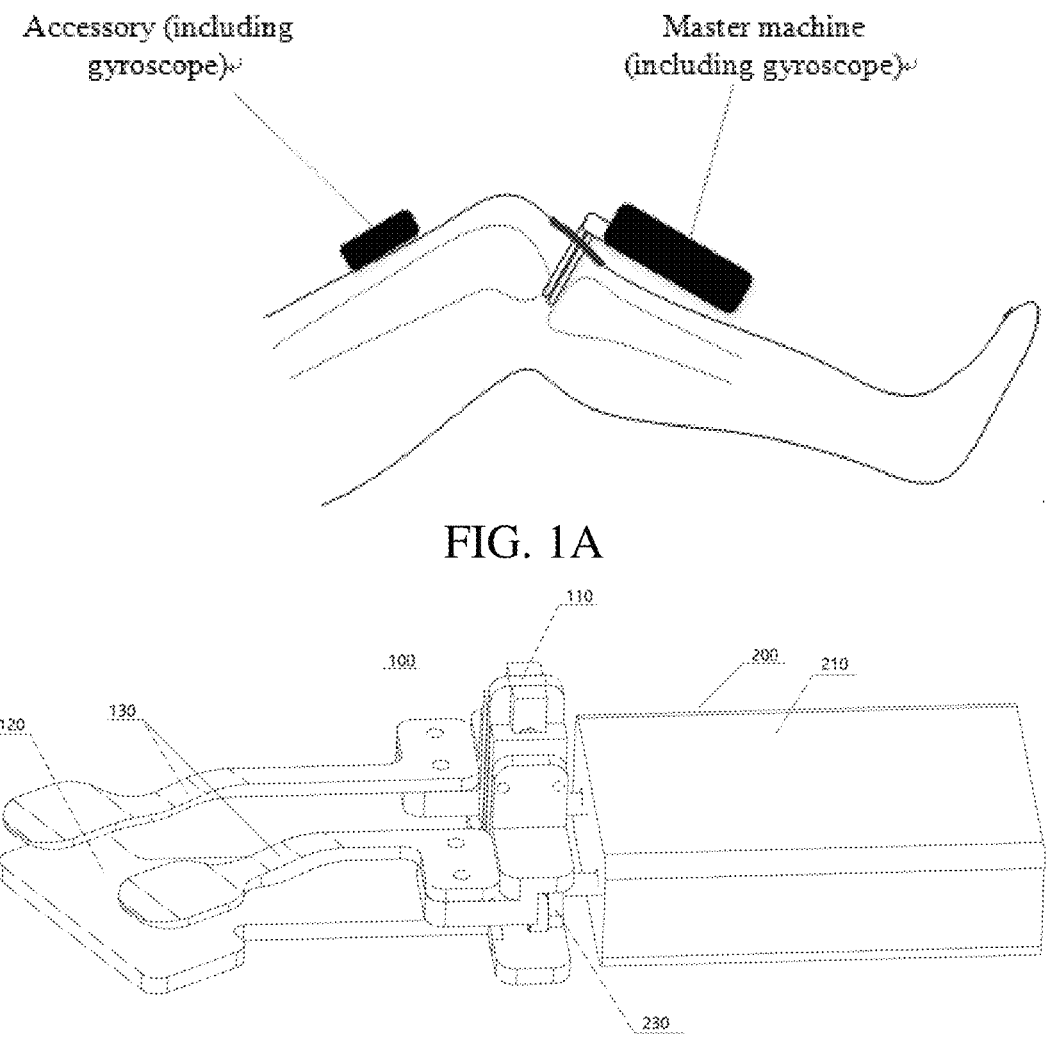
FIG. 1A illustrates a schematic diagram showing the installation of a knee-joint soft tissue balance measurement apparatus.
FIG. 1B illustrates a schematic perspective view of a master machine of the knee-joint soft tissue balance measurement apparatus.

Exemplary embodiments will now be described more thoroughly with reference to the accompanying drawings. However, the exemplary embodiments can be embodied in many forms and should not be construed as being limited to the embodiments set forth herein. On the contrary, these embodiments are provided to make the present application thorough and complete, and to fully convey the concept of the exemplary embodiments to a person skilled in the art. In the drawings, the same reference signs denote the same or similar parts, and therefore, their repeated description will be omitted.

The described features, structures or properties can be combined in one or more embodiments in any appropriate manner In the description below, many specific details are provided to present a thorough understanding of the embodiments of the present disclosure. However, a person skilled in the art will appreciate that the technical solutions of the present disclosure can be practiced without one or more of these specific details, or by using other means, components, materials, apparatuses, operations, etc. Under these circumstances, the commonly known structures, methods, apparatuses, implementations, materials, or operations will not be shown or described in detail.

The flow charts illustrated in the accompanying drawings are merely for exemplary explanation, and do not necessarily include all the content and operations/steps, nor do they have to be performed in an order as described. For example, some of the operations/steps can also be broken down, and some of the operations/steps can be combined or partially combined. Therefore, the actual order of execution may be changed according to the actual situation.

The terms "first", "second" and the like in the description, claims and above-mentioned drawings of the present application are for the purpose of distinguishing different objects, rather than describing a specific order. Furthermore, the terms "comprise" and "have" and any variations thereof are intended to cover non-exclusive inclusions. For example, a process, method, system, product or equipment including a series of steps or units is not limited to the listed steps or units, but optionally further includes unlisted steps or units, or optionally further includes other steps or units inherent to the process, method, product or equipment.

The present application provides a surgical upper computer, a knee-joint based soft tissue balance measurement apparatus, and a corresponding joint flexion angle measurement apparatus, which are used to acquire and exhibit the force and gap of soft tissues in the total knee arthroplasty in a reasonable manner, thereby helping a surgeon make a planned adjustment to reduce the number of osteotomy adjustments or the damage to ligaments while shortening the operation time.

A surgical upper computer for a total knee arthroplasty and a total knee arthroplasty system according to the embodiments of the present application will be illustrated in detail below with reference to the accompanying drawings.

FIG. 1A illustrates a schematic diagram showing the installation of a knee-joint soft tissue balance measurement apparatus.

As shown in FIG. 1A, after a pre-cut osteotomy is performed on the tibia and/or femur of a patient, a master machine of the measurement apparatus is placed between the tibia and the femur of the patient, and the accessory of the measurement apparatus is placed on an upper surface of the thigh of the patient.

According to some embodiments, a gap of the knee joint and the elasticity of soft tissues may also be measured by using a knee-joint soft tissue balance measurement apparatus after a prosthesis is implanted between the tibia and the femur of the patient and before an insert is implanted.

According to some embodiments, the master machine and the accessory may each include a gyroscope, which may be used to measure a joint flexion angle of the patient.

FIG. 1B illustrates a schematic perspective view of a master machine of the knee-joint soft tissue balance measurement apparatus.

As shown in FIG. 1B, the master machine of the measurement apparatus includes a measurement module 100 and a drive module 200.

The measurement module 100 includes a mounting base 110, a push plate 120 for butting the tibia, and a butting member 130 for butting the femur.

With reference to a viewing angle in FIG. 1B, the push plate is fixedly connected to the mounting base; the butting member is connected to the mounting base in such a way that it can move in a longitudinal direction relative to the mounting base; an upper butting plate portion of the butting member and a lower butting plate portion of the push plate extend approximately in parallel and perpendicular to the longitudinal direction; and the upper butting plate portion is arranged above the lower butting plate portion in the longitudinal direction.

The drive module 200 includes a hermetic housing 210, a power unit and an actuation mechanism 230.

The power unit is disposed in the hermetic housing, the actuation mechanism is disposed outside the hermetic housing; the power unit hermetically passes through the hermetic housing and is in transmission connection with the actuation mechanism; and the actuation mechanism is constructed to removably cooperate with the measurement module for pushing the butting member to move longitudinally relative to the push plate.

According to some embodiments, the butting member respectively acts on distal medial and lateral condyles of the femur to produce a medial pushing force and a lateral pushing force, and then form a medial gap and a lateral gap between the femur and the tibia.

The push plate is used for supporting the tibia to keep soft tissue balance.

FIG. 2 illustrates a flow chart of a first operating mode of a surgical upper computer according to an exemplary embodiment of the present application.

As shown in FIG. 2, in S101, by means of an interactive interface, information to be input is exhibited to a user. The information to be input includes a magnitude range and change interval of a pushing force applied between a femur and a tibia that are subjected to a pre-cut osteotomy.

According to some embodiments, the information to be input further includes the magnitude range and change interval of a pushing force applied between the femur and the tibia after the implantation of a knee joint prosthesis and before the implantation of an insert, so that whether the implanted knee joint prosthesis needs to be adjusted is determined.

According to some embodiments, the pre-cut osteotomy includes performing an osteotomy on the tibia and/or femur, to facilitate adjustment and correction during a process of implanting a knee joint prosthesis.

The interactive interface is shown as in FIG. 3A, and at the preset joint flexion angle, the information to be input includes an initial force, an ending force, and the step size of the force, which define the magnitude range and change interval of the pushing force applied between the femur and the tibia.

For example, if the initial force is set to 30 N, the ending force is set to 60 N and the step size is set to 5 N, the magnitude range of the pushing force is 30 N-60 N and the change interval is 5 N.

In S103, the butting member and the push plate are controlled to apply different pushing forces between the femur and the tibia at the preset joint flexion angle, and corresponding relationship data between the pushing force and a gap between the femur and the tibia are acquired.

For example, at the preset joint flexion angle, the initial force is set to 30 N, the ending force is set to 60 N and the step size is set to 5 N on the interactive interface; the surgical upper computer transmits an instruction to the measurement apparatus; and the butting member of the measurement apparatus respectively acts on the distal medial and lateral condyles of the femur to produce medial and lateral pushing forces, from (30, 30) N, to (30, 35) N, (30, 40) N . . . , till (60, 60) N, where a total of 49 medial and lateral pushing force combinations are produced, and 49 medial and lateral gap combinations are correspondingly obtained.

Generally, at the same joint flexion angle, if a user sets another different force range and change interval, a different number of pushing force combinations and the corresponding gap combinations can be produced.

Further, the joint flexion angle can be changed to a plurality of different joint flexion angles to acquire the pushing force combinations and the corresponding gap combinations with the knee joint at different angles.

In S105, the data values of the pushing force and corresponding gap are visually exhibited.

According to some embodiments, the data values of the pushing force and corresponding gap include, at different joint flexion angles, pushing force difference values between the medial pushing forces and the lateral pushing forces, gap difference values between the medial gaps and the lateral gaps, and the absolute values of the gaps.

Figure 3B:
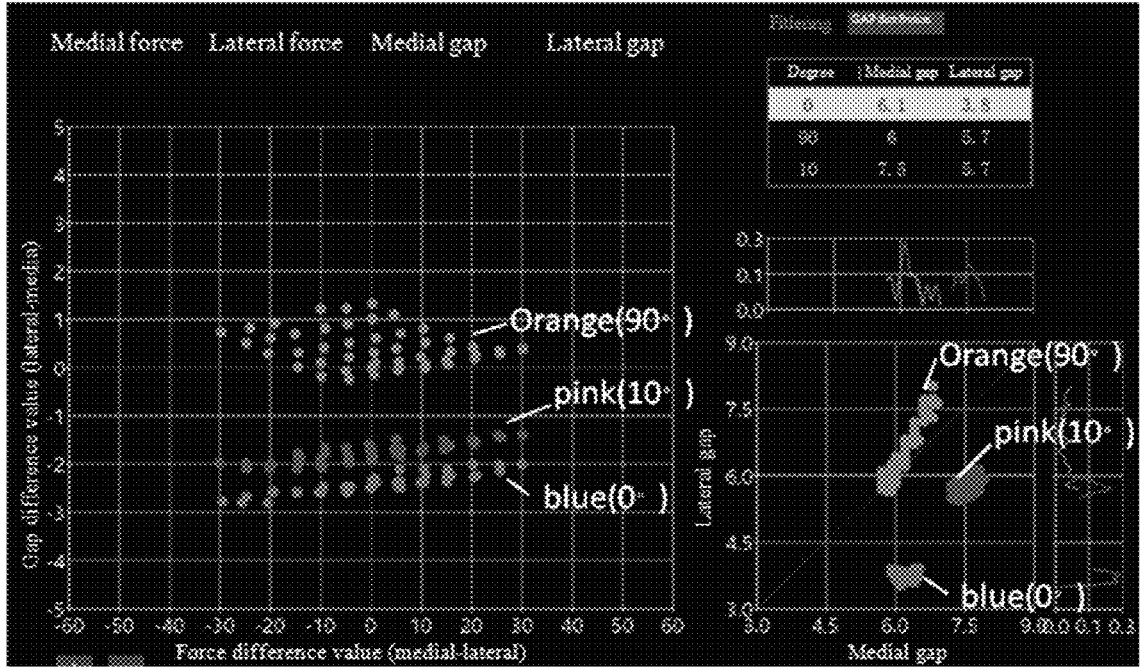
FIG. 3B illustrates a diagram exhibiting visualized information of a first operating mode of a surgical upper computer according to an exemplary embodiment of the present application.

As shown in FIG. 3B, the left panel is drawn according to the pushing force difference values and the gap difference values in the first operating mode, with the pushing force difference value (medial-lateral) as the abscissa and the gap difference value (medial-lateral) as the ordinate. It is used to exhibit whether the soft tissues of the knee joint of a patient achieve a balance status under the actions of the medial and lateral pushing forces.

The right panel is drawn according to the absolute values of the gap in the first operating mode, with the medial gap as the abscissa and the lateral gap as the ordinate. It is used to exhibit the values of the medial and lateral gaps formed by the medial and lateral pushing forces when the soft tissues of the knee joint of the patient achieve the balance status.

For example, when the joint flexion angle is 0°, data points in the drawing are shown in blue, and the medial and lateral gaps are 6.1 and 3.8 respectively when the soft tissues of the knee joint of the patient achieve the balance status-balance status.

When the joint flexion angle is 90°, data points in the drawing are shown in orange, and the medial and lateral gaps are 6 and 5.7 respectively when the soft tissues of the knee joint of the patient achieve the balance statusbalance status.

When the joint flexion angle is 10°, data points in the drawing are shown in pink, and the medial and lateral gaps are 7.5 and 5.7 respectively when the soft tissues of the knee joint of the patient achieve the balance status.

Generally, the distal femur has a medial condyle at the inner side of the knee joint and a lateral condyle at the outer side of the knee joint, and under different stretching states, a medial gap formed between the medial condyle and the tibia, a lateral gap formed between the lateral condyle and the tibia, and a force acting on corresponding soft tissues may be different.

FIG. 4 illustrates a flow chart of a second operating mode of a surgical upper computer according to an exemplary embodiment of the present application.

In S201, by means of a second interactive interface, second information to be input is exhibited to a user. The second information to be input includes a plurality of value ranges of the joint flexion angle and the data values, corresponding to the plurality of value ranges, of the pushing force applied between the femur and the tibia that are subjected to the pre-cut osteotomy.

The interactive interface is shown as in FIG. 5A, and in the second operating mode of the surgical upper computer, the second information to be input includes the value range of a preset joint flexion angle, as well as the data values of medial and lateral pushing forces.

For example, the value range of the joint flexion angle may be set to 0° to 135°.

According to some embodiments, when the femur and tibia of the patient are in a straight position, the joint flexion angle is calibrated to 0°, and postflexed to the maximum joint flexion angle.

According to the value range of the joint flexion angle, the data value of the pushing force is set as follows:

when the joint flexion angle is between 0° and 40°, the medial and lateral pushing forces are both set to 25 N;

when the joint flexion angle is between 41° and 80°, the medial and lateral pushing forces are both set to 50 N; and when the joint flexion angle is between 81° and 135°, the medial and lateral pushing forces are both set to 80 N.

The settings of the joint flexion angle and the pushing force may also be acquired according to a preset functional relationship. For example, the joint flexion angle is in a sinusoidal function relationship with the pushing force.

In S203, in response to information input by the user, the butting member and the push plate are controlled to apply corresponding pushing forces between the femur and the tibia respectively within the plurality of value ranges of the joint flexion angle, and the data values of the gap between the femur and the tibia are acquired.

The femur and tibia of the patient are adjusted multiple times according to the value range of the joint flexion angle; the surgical upper computer transmits an instruction to the measurement apparatus according to data on the second interactive interface; a pushing force is applied by means of the butting member and push plate of the measurement apparatus; and multiple measurements are performed to acquire the data values of the medial and lateral pushing forces, as well as the data values of the corresponding medial and lateral gaps.

For example, when the joint flexion angle is 120°, the medial and lateral pushing forces are both measured to be 80 N, and the corresponding medial and lateral gaps are 23.22 and 17.47 respectively.

In S205, a relationship between the data value of the pushing force and the joint flexion angle and a relationship between the data value of the gap and the joint flexion angle are visually exhibited.

Figure 5B:
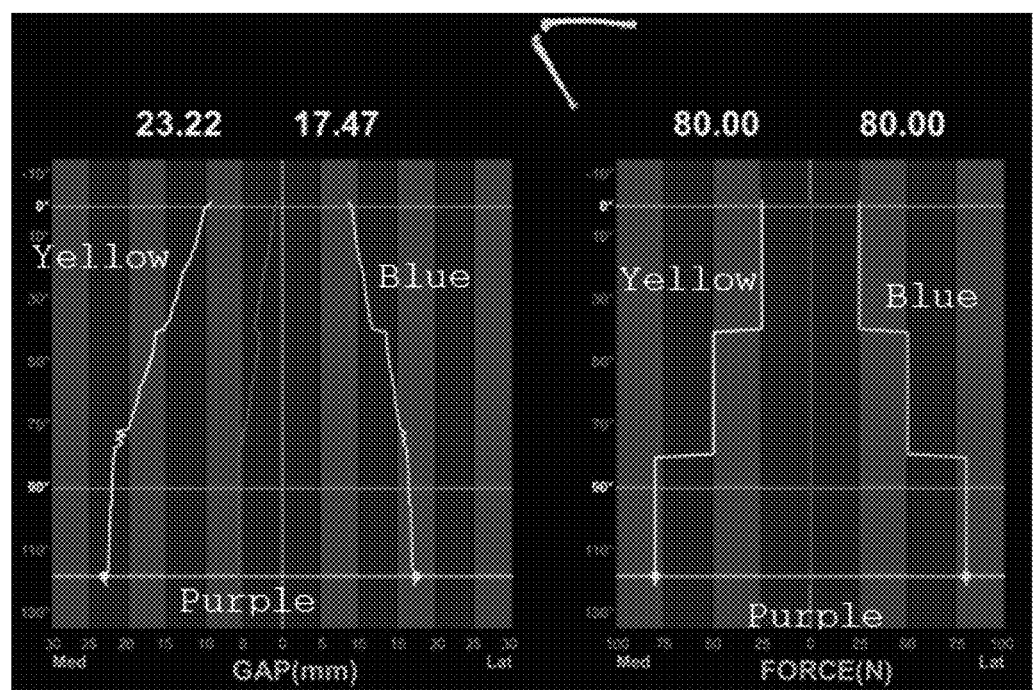
FIG. 5B illustrates a diagram exhibiting visualized information of a second operating mode of a surgical upper computer according to an exemplary embodiment of the present application.

As shown in FIG. 5B, the left panel illustrates the change curves of medial and lateral gaps of the knee joint in the second operating mode of the surgical upper computer, with the data value of the gap as the abscissa and the joint flexion angle as the ordinate, in which a yellow curve represents a medial gap, a blue curve represents a lateral gap, and a purple curve represents a gap difference value.

The right panel illustrates the change curves of a pushing force between the knee joint in the second operating mode of the surgical upper computer, with the data value of the pushing force as the abscissa and the joint flexion angle as the ordinate, in which a yellow curve represents a medial pushing force, a blue curve represents a lateral pushing force, and a purple curve represents a pushing force difference value.

FIG. 6 illustrates a flow chart of a third operating mode of a surgical upper computer according to an exemplary embodiment of the present application.

In S301, by means of a third interactive interface, third information to be input is exhibited to a user. The third information to be input includes a plurality of value ranges of the joint flexion angle and the data values, corresponding to the plurality of value ranges, of the gap formed between the femur and the tibia that are subjected to the pre-cut osteotomy.

The third interactive interface is shown as in FIG. 7A, and in the third operating mode of the surgical upper computer, the third information to be input includes the value range of a preset joint flexion angle, as well as the data values of medial and lateral gaps.

For example, the value range of the joint flexion angle may be set to 0° to 135°.

According to some embodiments, when the femur and tibia of the patient are in a straight position, the joint flexion angle is calibrated to 0°, and postflexed to the maximum joint flexion angle.

According to the value range of the joint flexion angle, the data value of the gap is set as follows:

when the joint flexion angle is between 0° and 40°, the medial and lateral gaps are both set to 6;

when the joint flexion angle is between 41° and 80°, the medial and lateral gaps are both set to 10; and when the joint flexion angle is between 81° and 135°, the medial and lateral gaps are both set to 16.

The settings of the joint flexion angle and the gap may also be acquired according to a preset functional relationship. For example, the joint flexion angle is in a sinusoidal function relationship with the gap.

In S303, in response to information input by the user, the butting member and the push plate are controlled to form corresponding gaps between the femur and the tibia respectively within the plurality of value ranges of the joint flexion angle, and the data values of the pushing force between the femur and the tibia are acquired.

The femur and tibia of the patient are adjusted multiple times according to the value range of the joint flexion angle; the surgical upper computer transmits an instruction to the measurement apparatus according to data on the interactive interface; a pushing force is applied by means of the butting member and push plate of the measurement apparatus; and multiple measurements are performed to acquire the data values of the medial and lateral gaps, as well as the data values of the corresponding medial and lateral pushing forces.

For example, when the joint flexion angle is 120°, the medial and lateral gaps are both measured to be 16, and the corresponding medial and lateral pushing forces are 73.00 N and 93.50 N respectively.

In S305, a relationship between the data value of the pushing force and the joint flexion angle and a relationship between the data value of the gap and the joint flexion angle are visually exhibited.

Figure 7B:
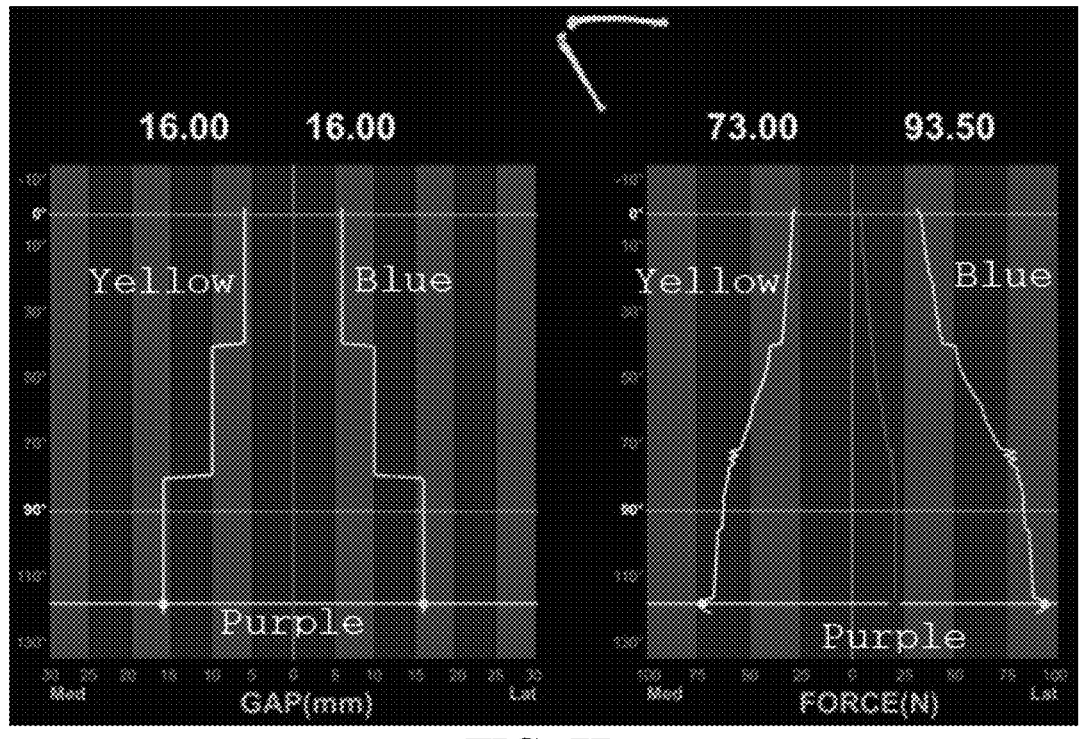
FIG. 7B illustrates a diagram exhibiting visualized information of a third operating mode of a surgical upper computer according to an exemplary embodiment of the present application.

As shown in FIG. 7B, the left panel illustrates the change curves of medial and lateral gaps of the knee joint in the third operating mode of the surgical upper computer, with the data value of the gap as the abscissa and the joint flexion angle as the ordinate, in which a yellow curve represents a medial gap, a blue curve represents a lateral gap, and a purple curve represents a gap difference value.

The right panel illustrates the change curves of a pushing force between the knee joint in the third operating mode of the surgical upper computer, with the data value of the pushing force as the abscissa and the joint flexion angle as the ordinate, in which a yellow curve represents a medial pushing force, a blue curve represents a lateral pushing force, and a purple curve represents a pushing force difference value.

FIG. 8 illustrates a flow chart of a fourth operating mode of a surgical upper computer according to an exemplary embodiment of the present application.

In S401, by means of a fourth interactive interface, fourth information to be input is exhibited to a user. The fourth information to be input includes the value range of the joint flexion angle and the data value of a fixed pushing force applied between the femur and the tibia that are subjected to the pre-cut osteotomy.

The fourth interactive interface is shown as in FIG. 5A, and in the fourth operating mode of the surgical upper computer, the fourth information to be input includes the value range of a preset joint flexion angle, as well as the data values of medial and lateral pushing forces.

For example, the value range of the joint flexion angle is between 0° and 135°, and at any joint flexion angle within the value range, the medial and lateral pushing forces are both set to a fixed value of 18 N.

In S403, in response to information input by the user, the butting member and the push plate are controlled to apply a fixed pushing force between the femur and the tibia within the value range of the joint flexion angle, and the data value of the gap between the femur and the tibia is acquired.

The femur and tibia of the patient are adjusted multiple times according to the value range of the joint flexion angle; the surgical upper computer transmits an instruction to the measurement apparatus according to data on the interactive interface; a pushing force is applied by means of the butting member and push plate of the measurement apparatus; and multiple measurements are performed to acquire the data values of the medial and lateral pushing forces, as well as the data values of the corresponding medial and lateral gaps.

For example, when the joint flexion angle is 96°, the medial and lateral pushing forces are measured to be 18.60 N and 18.90 N respectively, and the corresponding medial and lateral gaps are 13.50 and 12.10 respectively.

Generally, the measurement apparatus vibrates due to interference factors (such as the friction between contact surfaces) in actual use, resulting in a possible error occurring to the actually measured data (the actually measured medial and lateral pushing forces) as compared with theoretical values (the medial and lateral pushing forces set to fixed values in the surgical upper computer).

In S405, a relationship between the data value of the fixed pushing force and the joint flexion angle and a relationship between the data value of the gap and the joint flexion angle are visually exhibited.

Figure 9:
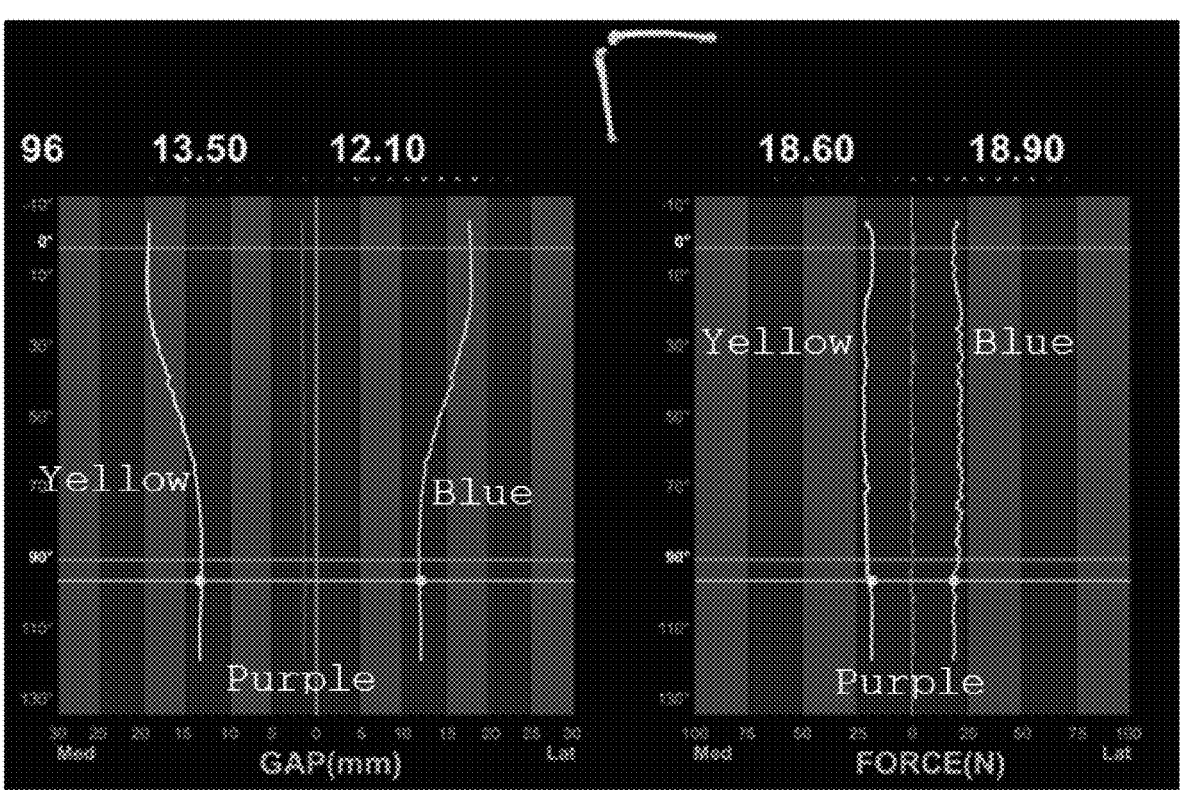
FIG. 9 illustrates a diagram exhibiting visualized information of a fourth operating mode of a surgical upper computer according to an exemplary embodiment of the present application.

As shown in FIG. 9, the left panel illustrates the change curves of medial and lateral gaps of the knee joint in the fourth operating mode of the surgical upper computer, with the data value of the gap as the abscissa and the joint flexion angle as the ordinate, in which a yellow curve represents a medial gap, a blue curve represents a lateral gap, and a purple curve represents a gap difference value.

The right panel illustrates the change curves of a pushing force between the knee joint in the fourth operating mode of the surgical upper computer, with the data value of the pushing force as the abscissa and the joint flexion angle as the ordinate, in which a yellow curve represents a medial pushing force, a blue curve represents a lateral pushing force, and a purple curve represents a pushing force difference value.

FIG. 10 illustrates a flow chart of a fifth operating mode of a surgical upper computer according to an exemplary embodiment of the present application.

In S501, by means of a fifth interactive interface, fifth information to be input is exhibited to a user. The fifth information to be input includes the value range of the joint flexion angle and the data value of a fixed gap formed between the femur and the tibia that are subjected to the pre-cut osteotomy.

A reference may be made to FIG. 7A for the fifth interactive interface, and in the fifth operating mode of the surgical upper computer, the fifth information to be input includes the value range of a preset joint flexion angle, as well as the data values of medial and lateral gaps.

For example, the value range of the joint flexion angle is between 0° and 135°, and at any joint flexion angle within the value range, the medial and lateral gaps are both set to a fixed value of 12.

In S503, in response to information input by the user, the butting member and the push plate are controlled to form a fixed gap between the femur and the tibia within the value range of the joint flexion angle, and the data value of the pushing force between the femur and the tibia is acquired.

The femur and tibia of the patient are adjusted multiple times according to the value range of the joint flexion angle; the surgical upper computer transmits an instruction to the measurement apparatus according to data on the interactive interface; a pushing force is applied by means of the butting member and push plate of the measurement apparatus; and multiple measurements are performed to acquire the data values of the medial and lateral gaps, as well as the data values of the corresponding medial and lateral pushing forces.

For example, when the joint flexion angle is 120°, the medial and lateral gaps are both measured to be 12.00, and the corresponding medial and lateral pushing forces are 57.70 N and 57.70 N respectively.

Generally, the measurement apparatus vibrates due to interference factors (such as the friction between contact surfaces) in actual use, resulting in a possible error occurring to the actually measured data (the actually measured medial and lateral pushing forces) as compared with theoretical values (the corresponding medial and lateral pushing forces acquired according to the medial and lateral gaps that are set to be fixed values in the surgical upper computer).

In S505, a relationship between the data value of the pushing force and the joint flexion angle and a relationship between the data value of the fixed gap and the joint flexion angle are visually exhibited.

Figure 11:
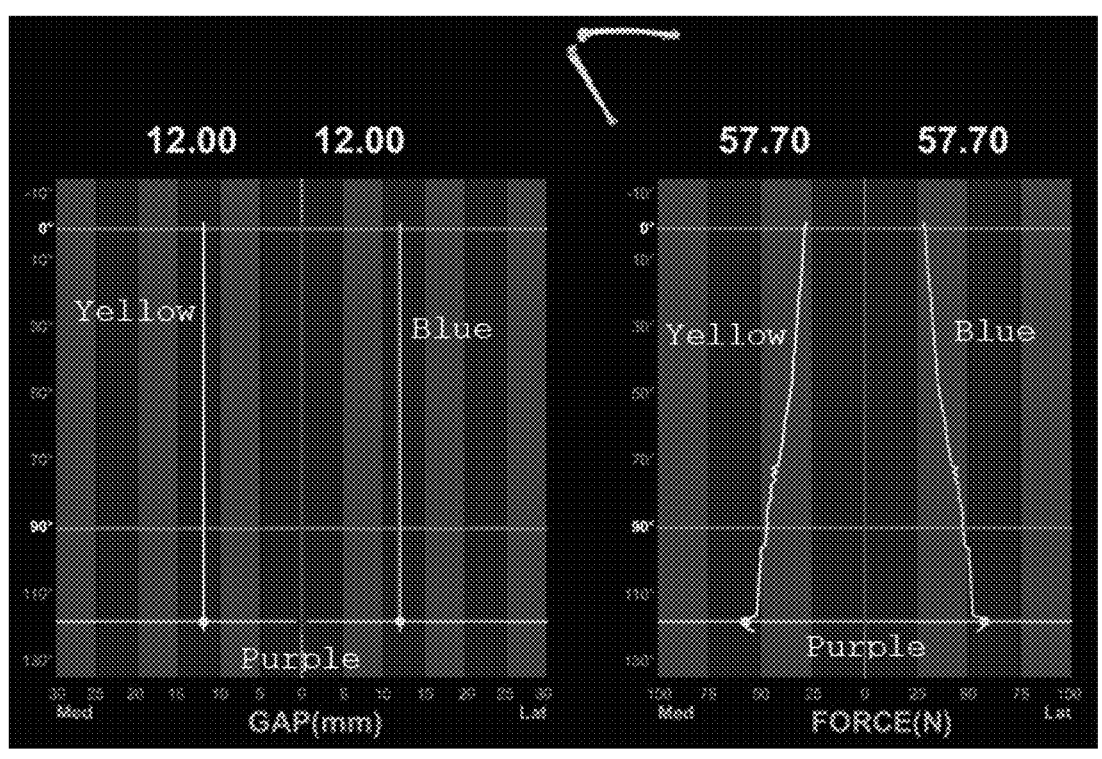
FIG. 11 illustrates a diagram exhibiting visualized information of a fifth operating mode of a surgical upper computer according to an exemplary embodiment of the present application.

As shown in FIG. 11, the left panel illustrates the change curves of medial and lateral gaps of the knee joint in the fifth operating mode of the surgical upper computer, with the data value of the gap as the abscissa and the joint flexion angle as the ordinate, in which a yellow curve represents a medial gap, a blue curve represents a lateral gap, and a purple curve represents a gap difference value.

The right panel illustrates the change curves of a pushing force between the knee joint in the fifth operating mode of the surgical upper computer, with the data value of the pushing force as the abscissa and the joint flexion angle as the ordinate, in which a yellow curve represents a medial pushing force, a blue curve represents a lateral pushing force, and a purple curve represents a pushing force difference value.

Figure 12:
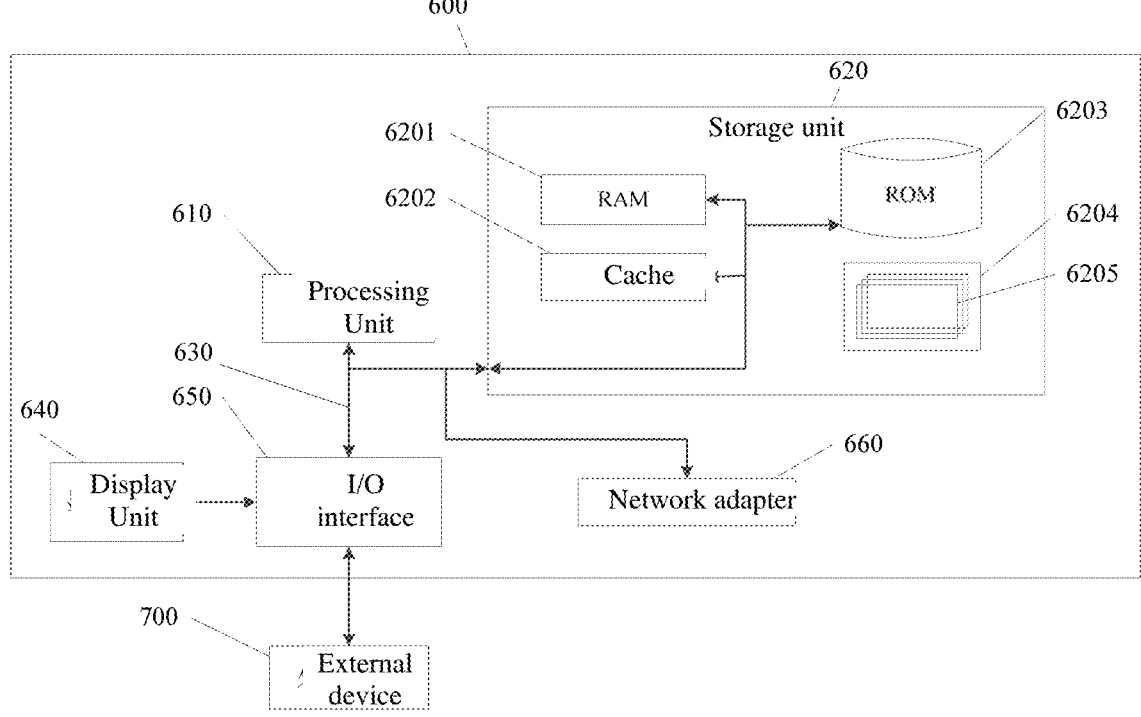
FIG. 12 illustrates a block diagram of a surgical upper computer according to an exemplary embodiment of the present application.

FIG. 12 illustrates a block diagram of a surgical upper computer according to an exemplary embodiment of the present application.

As shown in FIG. 12, an electronic device 600 is merely an example, and should not impose any limitation to the function and application range of the embodiments of the present application.

As shown in FIG. 12, the electronic device 600 is embodied in the form of a general-purpose computing device. The electronic device 600 may include but are not limited to the following components: at least one processing unit 610, at least one storage unit 620, a bus 630 connecting different system components (including the storage unit 620 and the processing unit 610), a display unit 640, etc. The storage unit stores a program code, which can be executed by the processing unit 610 such that the processing unit 610 executes the methods according to various exemplary embodiments of the present application as described in the description. For example, the processing unit 610 may execute the method as shown in FIG. 2.

The storage unit 620 may include a readable medium in the form of a volatile storage unit, for example, a random access memory (RAM) 6201 and/or a cache memory 6202, and may further include a read-only memory (ROM) 6203.

The storage unit 620 may further include a program/utility 6204 having a set of (at least one) program modules 6205, which include, but are not limited to: an operating system, one or more application programs, other program modules and program data. Each of or a combination of these examples may include the implementation of a network environment.

The bus 630 may represent one or more of several types of bus structures, including a storage unit bus or a storage unit controller, a peripheral bus, a graphics acceleration port, a processing unit, or a local area bus using any of a variety of bus structures.

The electronic device 600 may also communicate with one or more external devices 700 (for example, a keyboard, a pointing device, a Bluetooth device, etc.), and may also communicate with one or more devices that enables a user to interact with the electronic device 600, and/or communicate with any device (for example, a router, a modem, etc.) that enables the electronic device 600 to communicate with one or more other computing devices. Such communication may be performed via an input/output (I/O) interface 650. Moreover, the electronic device 600 may also communicate with one or more networks (for example, a local area network (LAN), a wide area network (WAN), and/or a public network, such as the Internet) via a network adapter 660. The network adapter 660 may communicate with other modules of the electronic device 600 via the bus 630. It should be understood that, although not illustrated in the drawings, other hardware and/or software modules used in combination with the electronic device 600 may include, but are not limited to: a microcode, a device driver, a redundant processing unit, an external disk drive array, a RAID system, a tape driver and a data backup storage system, etc.

From the description of the above embodiments, a person skilled in the art can easily understand that the exemplary embodiments described herein may be implemented by software, or by combining the software with necessary hardware. The technical solutions according to the embodiments of the present application may be embodied in the form of software products, which may be stored in a non-volatile storage medium (which may be a CD-ROM, a USB flash disk, a mobile hard disk, etc.) or on the network and may include several instructions to enable a computing device (which may be a personal computer, a server, a mobile terminal, or a network device, etc.) to execute the method according to the embodiment of the present application.

The software product may be a readable medium or a combination of several readable mediums. The readable medium may be a readable signal medium or a readable storage medium. The readable storage medium may be, for example, but not limited to, electric, magnetic, optical, electromagnetic, infrared, or semiconductor systems, apparatuses or device, or a combination of any of the above. More specific examples (non-exhaustive list) of the readable storage medium include: an electric connection having one or more wires, a portable disk, a hard disk, a random-access memory (RAM), a read-only memory (ROM), an erasable programmable read-only memory (EPROM or flash memory), an optical fiber, a portable compact disk read-only memory (CD-ROM), an optical storage device, a magnetic storage device, or any suitable combination of the above.

A computer-readable storage medium may include a data signal propagated in a baseband or as part of a carrier, and a readable program code is carried in the data signal. Such a propagated data signal may be in a variety of forms, including but not limited to an electromagnetic signal, an optical signal, or any suitable combination of the above. The readable storage medium may also be any readable medium other than a readable storage medium, and this readable medium may transmit, propagate, or transport a program that is used by or in combination with an instruction execution system, apparatus, or device. A program code contained in the readable storage medium may be transmitted by using any suitable medium, which includes, but is not limited to, wireless means, wired means, optical fiber cables, RF, etc., or any suitable combination of the above.

The program code for executing the operations in the present application may be written in one or any combination of multiple programming languages, which include object-oriented programming languages, such as Java, C++, etc., and further include conventional procedural programming languages, such as "C" language or similar programming languages. The program code may be executed completely on the computing device of a user, partially on user equipment, as a stand-alone software package, partially on the computing device of the user and partially on a remote computing device, or completely on the remote computing device or server. In a situation where the remote computing device is involved, the remote computing device may be connected to the computing device of the user through any networks, including a local area network (LAN) or a wide area network (WAN), or may be connected to an external computing device (for example, via Internet by using an Internet service provider).

The above-mentioned computer-readable medium carries one or more programs which, when executed by one of the devices, enables the computer-readable medium to implement the foregoing functions.

A person skilled in the art can understand that the above-mentioned modules can be either distributed in the apparatus according to the description of the embodiment, or changed accordingly to be disposed in one or more apparatuses that are different from this embodiment. The modules in the above-mentioned embodiments can be combined into one module, or may be further split into a plurality of sub-modules.

According to some embodiments of the present application, the angle, force and gap between the knee joint can be quantified and reasonably exhibited in the present application to facilitate the surgical operation of a surgeon and reduce the damage to a patient caused by ligament releasing, such that whether the soft tissue balance is achieved can be determined quickly and the service life of a prosthesis can be prolonged.

The embodiments of the present application are described in detail above. The description of the embodiments above is merely for the purpose of helping understand the methods and their core concepts of the present application. Meanwhile, alternations or variations made by those skilled in the art in accordance with the concept of the present application and based on the specific embodiments and application scope of the present application shall fall within the protection scope of the present application. In summary, the content of the description should not be understood as a limitation to the present application.

What is claimed is:

1. A surgical upper computer for controlling a knee-joint soft tissue balance measurement apparatus and performing data acquisition in a total knee arthroplasty, the measurement apparatus comprising a master machine and an accessory, the master machine comprising a butting member respectively acting on distal medial and lateral condyles of a femur and a push plate supporting a tibia, the surgical upper computer comprising:

a processor; and a memory, storing a computer program which, when executed by the processor, enables the processor to execute a first operating mode of the surgical upper computer, the first operating mode comprising:

exhibiting, by an interactive interface, to a user, first information to be input, the first information to be input comprising a magnitude range and change interval of a pushing force applied between a femur and a tibia;

in response to information input by the user, controlling the butting member and the push plate to apply different pushing forces between the distal medial and lateral condyles of the femur and the tibia at a first preset joint flexion angle to produce a first set of multiple medial and lateral pushing force combinations, acquiring a first set of multiple medial and lateral gap combinations correspondingly, and acquiring a first corresponding relationship data between the pushing force and a gap between the femur and the tibia; controlling the butting member and the push plate to apply different pushing forces between the distal medial and lateral condyles of the femur and the tibia at a second preset joint flexion angle to produce a second set of multiple medial and lateral pushing force combinations, acquiring a second set of multiple medial and lateral gap combinations correspondingly, and acquiring a second corresponding relationship data between the pushing force and a gap between the femur and the tibia; and visually exhibiting the corresponding relationship data.

2. The surgical upper computer according to claim 1, wherein the information to be input comprising the magnitude range and change interval of the pushing force applied between the femur and the tibia, comprises:

a magnitude range and change interval of a pushing force applied between a femur and a tibia having subjected to a pre-cut osteotomy; or a magnitude range and change interval of a pushing force applied between a femur and a tibia after prosthesis implantation and before spacer implantation.

3. The surgical upper computer according to claim 1, wherein controlling the butting member and the push plate to apply different pushing forces between the femur and the tibia at a preset joint flexion angle, comprises:

controlling the butting member and the push plate to apply different pushing forces between the femur and the tibia respectively at a plurality of different preset joint flexion angles.

4. The surgical upper computer according to claim 1, wherein the corresponding relationship data comprises difference values between the pushing forces and corresponding difference values and absolute values of the gaps.

5. The surgical upper computer according to claim 1, when executed by the processor, the computer program enables the processor to execute a second operating mode of the surgical upper computer, and the second operating mode comprises:

exhibiting, by the interactive interface, to the user, second information to be input, the second information to be input comprising a dynamic change range of the preset joint flexion angle, and a relationship between the preset joint flexion angle and the pushing force applied between the femur and the tibia;

in response to information input by the user, controlling the butting member and the push plate to apply corresponding pushing forces between the femur and the tibia during a process of dynamically adjusting the joint flexion angle within the dynamic change range to adjust the femur and the tibia, and acquiring data values of the gap between the femur and the tibia; and at least visually exhibiting a relationship between the data value of the gap and the joint flexion angle.

6. The surgical upper computer according to claim 5, wherein the dynamic change range of the preset joint flexion angle, and a relationship between the preset joint flexion angle and the pushing force applied between the femur and the tibia, comprise:

a plurality of value ranges set according to the dynamic change range, and data values of the pushing force corresponding to the plurality of value ranges; or the dynamic change range of the preset joint flexion angle, and a functional relationship between the preset joint flexion angle and the pushing force.

7. The surgical upper computer according to claim 6, wherein when a plurality of value ranges is set according to the dynamic change range of the preset joint flexion angle, the pushing forces corresponding to different value ranges of the preset joint flexion angle have different data values.

8. The surgical upper computer according to claim 5, when executed by the processor, the computer program enables the processor to execute a third operating mode of the surgical upper computer, and the third operating mode comprises:

exhibiting, by the interactive interface, to the user, third information to be input, the third information to be input comprising the dynamic change range of the preset joint flexion angle, and a data value of a fixed pushing force applied between the femur and the tibia;

in response to information input by the user, controlling the butting member and the push plate to apply the fixed pushing force between the femur and the tibia during a process of dynamically adjusting the joint flexion angle within the dynamic change range to adjust the femur and the tibia, and acquiring data values of the gap between the femur and the tibia; and at least visually exhibiting a relationship between the data values of the gap and the joint flexion angle.

9. A total knee arthroplasty system, comprising the surgical upper computer of claim 1 and a knee-joint soft tissue balance measurement apparatus, wherein the measurement apparatus comprises a master machine and an accessory, the master machine comprises a butting member respectively acting on distal medial and lateral condyles of a femur and a push plate supporting a tibia.

* * * * *